United States Patent [19]
Moffett et al.

[11] Patent Number: 5,853,616
[45] Date of Patent: *Dec. 29, 1998

[54] METHOD FOR PREPARING LOW-CONCENTRATION POLYALUMINOSILICATE MICROGELS

[75] Inventors: Robert Harvey Moffett, Landenberg, Pa.; John Derek Rushmere, Wilmington, Del.

[73] Assignee: E. I. du Pont de Nemours and Company, Wilmington, Del.

[*] Notice: The term of this patent shall not extend beyond the expiration date of Pat. No. 5,648,055.

[21] Appl. No.: 874,141

[22] Filed: Jun. 13, 1997

Related U.S. Application Data

[63] Continuation-in-part of Ser. No. 548,224, Oct. 25, 1995, Pat. No. 5,648,055, which is a continuation-in-part of Ser. No. 345,890, Nov. 28, 1994, Pat. No. 5,503,820, which is a continuation-in-part of Ser. No. 166,679, Dec. 16, 1993, abandoned, which is a continuation-in-part of Ser. No. 093,157, Jul. 23, 1993, Pat. No. 5,312,595, which is a division of Ser. No. 887,793, May 26, 1992, Pat. No. 5,279,807.

[51] Int. Cl.$^6$ .................................................. C01B 33/26
[52] U.S. Cl. ...................................... 252/315.5; 423/330.1
[58] Field of Search ............................ 423/328.1, 330.1; 252/315.5

[56] References Cited

U.S. PATENT DOCUMENTS

| | | | |
|---|---|---|---|
| 2,217,466 | 10/1940 | Baylis | 210/23 |
| 2,234,285 | 3/1941 | Schworm et al. | 210/23 |
| 2,310,009 | 2/1943 | Baker et al. | 210/23 |
| 2,444,774 | 7/1948 | Hay | 210/23 |
| 2,466,842 | 4/1949 | Elston | 252/313 |
| 2,769,785 | 11/1956 | Walker | 252/359 |
| 4,213,950 | 7/1980 | Mahler | 423/329 |
| 4,554,211 | 11/1985 | Akira et al. | 428/402 |
| 4,954,220 | 9/1990 | Rushmore | 162/168.3 |
| 5,066,420 | 9/1991 | Chevallier | 252/313.2 |
| 5,176,891 | 1/1993 | Rushmore | 423/328.1 |
| 5,648,055 | 7/1997 | Moffett et al. | 423/328.1 |

FOREIGN PATENT DOCUMENTS

| | | |
|---|---|---|
| 584727 | 10/1959 | Canada . |
| 0359552 | 3/1990 | European Pat. Off. . |
| 0270289 | 7/1989 | Germany . |
| 827586 | 2/1960 | United Kingdom . |
| 1044019 | 9/1966 | United Kingdom . |
| 1300946 | 12/1972 | United Kingdom . |
| WO91/07350 | 5/1991 | WIPO . |

OTHER PUBLICATIONS

Reynold C. Merrill, Activated Silica Sols in Water Treatment, 40, 1355–1359 No date.
Reynold C. Merrill, Activated Silica—A New Chemical Eng Tool, 1, No. 1, 27–32, 1947 No month.
L.L. Klinger, Improvements in the Coagulation of Surface Waters with Activated Silica, 122, 40–50, 1946 No month.

*Primary Examiner*—Michael Lewis
*Assistant Examiner*—Stuart L. Hendickson

[57] ABSTRACT

An improved method and apparatus for preparing low-concentration polyaluminosilicate microgels from a water soluble silicate and an alkali metal aluminate in which the silicate and the aluminate are mixed at a rate to produce a Reynolds number of at least 4000, the mixture is aged and then diluted to a silica concentration of not more than 1.0 wt. %. The method achieves reduced silica deposition during the preparation of the microgels.

3 Claims, 4 Drawing Sheets

METHOD FOR PREPARING LOW-CONCENTRATION POLYALUMINOSILICATE MICROGELS

RELATED U.S. APPLICATIONS

This application is a continuation-in-part of application U.S. Ser. No. 08/548,224, filed Oct. 25, 1995, now U.S. Pat. No. 5,648,055 which was a continuation-in-part of application U.S. Ser. No. 08/345,890, filed Nov. 28, 1994, now U.S. Pat. No. 5,503,820 which was a continuation-in-part of U.S. Ser. No. 08/166,679, filed Dec. 16, 1993, abandoned, which application was a continuation-in-part of Ser. No. 08/093,159, filed on Jul. 23, 1993, U.S. Pat. No. 5,312,595, which was a divisional of Ser. No. 07/887,773, filed on May 26, 1993 U.S. Pat. No. 5,279,807.

BACKGROUND OF THE INVENTION

The present invention relates to an improved method and apparatus for preparing low-concentration polysilicate microgels, i.e., aqueous solutions having an active silica concentration of generally less than about 1.0 wt. %, which are formed by the partial gelation of an alkali metal silicate or a polysilicate, such as sodium polysilicate, having in its most common form one part $Na_2O$ to 3.3 parts $SiO_2$ by weight. The microgels, which are referred to as "active" silica in contrast to commercial colloidal silica, comprise solutions of from 1 to 2 nm diameter linked silica particles which have a surface area of at least about 1000 $m^2/g$. The particles are linked together during preparation, i.e., during partial gelation, to form aggregates which are arranged into three-dimensional networks and chains. The polysilicate microgels can be further modified by the incorporation of aluminum oxide into their structure. Such alumina modified polysilicates are classified as polyaluminosilicate microgels and are readily produced by a modification of the basic method for polysilicate microgels. A critical aspect of the invention is the ability to produce the microgels within a reasonable time period, i.e., not longer than about 15 minutes until the microgel is ready for use, without the risk of solidification and with minimum formation of undesirable silica deposits within the processing equipment. In this connection, the incorporation of alumina into the polysilicate microgel has been found beneficial in that it increases the rate of microgel formation. Polysilicate microgels produced according to the invention are particularly useful in combinations with water soluble cationic polymers as a drainage and retention aid in papermaking. At low pH values, below pH of 5, these products are more appropriately referred to as polysilicic acid microgels. As the pH value is raised, these products can contain mixtures of polysilicic acid and polysilicate microgels; the ratio being pH-dependent. For sake of convenience, these products hereinafter will be referred to as polysilicate microgels.

SUMMARY OF THE INVENTION

The present invention is an improved method and apparatus for continuously preparing a low-concentration polysilicate microgel which comprises: (a) simultaneously introducing a first stream comprising a water soluble silicate solution and a second stream comprising a strong acid having a pKa less than 6 into a mixing zone where the streams converge at an angle of not less than 30 degrees and at a rate sufficient to produce a Reynolds number of at least about 4000 and a resulting silicate/acid mixture having a silica concentration in the range of from about 1.0 to 6.0 wt. % and a pH in the range of from 2 to 10.5; (b) aging the silicate/acid mixture for a period of time sufficient to achieve a desired level of partial gelation (i.e., forming the microgel), usually for at least 10 seconds but not more than about 15 minutes; and (c) diluting the aged mixture to a silica concentration of not greater than about 2.0 wt. % whereby gelation is stabilized. To produce polyaluminosilicate microgels, a water soluble aluminum salt is added first to the acid stream prior to mixing it with the silicate stream. Alternatively, polyaluminosilicates can be prepared by mixing an alkali metal aluminate directly with the silicate stream with a resulting pH of generally above pH 8 and most typically above pH 10.

For best results, the silica concentration of the water soluble silicate starting solution is in the range of from 2 to 10 wt. % silica, and the concentration of the strong acid (e.g., sulfuric acid) is in the range of from 1 to 20 wt. % acid as the two streams are being introduced into the mixing zone. The preferred conditions in the mixing zone are a Reynolds number greater than 6000, a silica concentration in the range of 1.5 to 3.5 wt. % and a pH in the range of 7 to 10. The most preferred conditions are a Reynolds number greater than 6000, silica concentration of 2 wt. % and a pH of 9. The preparation of alumina modified microgel is best conducted by adding a soluble aluminum salt to the acid stream in an amount ranging from about 0.1 wt. % up to the solubility limit of the aluminum salt. The most useful polyaluminosilicate microgels prepared by adding an aluminum salt to the acid stream are those prepared with an $Al_2O_3/SiO_2$ mole ratio ranging from 1:1500 to 1:25 and, preferably, from 1:1250 to 1:50. Polyaluminosilicates prepared by reacting an alkali metal aluminate directly with the silicate can have $Al_2O_3/SiO_2$ mole ratios ranging up to about 1:4.

The apparatus according to the invention comprises: (a) a first reservoir for containing a water soluble silicate solution; (b) a second reservoir for containing a strong acid having a pKa of less than 6; (c) a mixing device having a first inlet which communicates with said first reservoir, a second inlet arranged at an angle of at least 30 degrees with respect to said first inlet which communicates with said second reservoir, and an exit; (d) a first pumping means located between said first reservoir and said mixing device for pumping a stream of silicate solution from said first reservoir into said first inlet, and first control means for controlling the concentration of silica in said silicate solution while said solution is being pumped such that the silica concentration in the exit solution from the mixing device is in the range of 1 to 6 wt. %; (e) a second pumping means located between said second reservoir and said mixing device for pumping a stream of acid from said second reservoir into said second inlet at a rate relative to the rate of said first pumping means sufficient to produce a Reynolds number within said mixing device of at least 4000 in the region where the streams converge whereby said silicate and said acid are thoroughly mixed; (f) mixture control means located within said exit and responsive to the flow rate of said acid into said mixing device for controlling the pH of the silicate/acid mixture in the range of from 2 to 10.5; (g) a receiving tank; (h) an elongated transfer loop which communicates with the exit of said mixing device and said receiving tank for transferring said mixture therebetween; (i) a dilution means for diluting the silicate/acid mixture in the receiving tank to a silica concentration of not more than 1.0 wt. %; (j) a fourth reservoir for containing a water soluble aluminum salt; (k) a fourth pumping device for introducing the aluminum salt into the acid stream; and (l) a control valve responsive to the aluminum salt flow and linked in parallel with the silicate control valve, and located between the fourth pumping device and the point of introduction of the aluminum salt into the acid stream.

In an alternative embodiment, polyaluminosilicates can be prepared by reacting an aluminate directly with the silicate by replacing the strong acid in reservoir (b) with sodium aluminate and using the second pumping means (e) to pump the aluminate into mixing device (c). Additionally, when preparing polyaluminosilicates using this procedure, the pH control device (f) can be eliminated and the silicate and aluminate flow can be controlled by volumetric flow rates, thus controlling the concentration of aluminate which is incorporated into the polyaluminosilicate microgel.

In an alternate embodiment, the apparatus of the invention includes a NaOH reservoir and means for periodically flushing the production system with warm NaOH which has been heated to a temperature of from 40° to 60° C. whereby deposits of silica can be solubilized and removed.

In a further embodiment of the invention, an agitating gas stream such as a stream of air or nitrogen or other inert gas can be introduced into the mixing device described by means of an additional inlet located at or near the mixing junction. Gas agitation provides an important industrial benefit in that it permits low silicate flow rates to be employed while maintaining the required turbulence and Reynolds number in the mixing zone.

In yet a further embodiment of this invention, mixing of the water soluble silicate solution either with an aluminate or with acid or with an aluminum salt and acid can be accomplished in an annular mixing device. This device can be an internal pipe or tube which protrudes into and subsequently discharges inside of a larger pipe or tube. The internal pipe discharge point is usually, but not necessarily, concentrically located inside the external pipe. One of the two fluids to be mixed is fed into the internal pipe. The second fluid is fed into the external pipe and flows around the outside of the internal pipe. Mixing of the two fluids occurs where the first fluid exits the internal pipe and combines with the second fluid in the larger external pipe. Usually, the acid and the aluminum salt solution are premixed prior to being fed into one of the pipes.

For the purpose of mixing the two liquids, the water soluble silicate solution and the acid or the alkali metal aluminate can be fed to either the internal or the external pipes at rates sufficient such that when the two streams are combined, a Reynolds number of greater than 4000 is produced in the mixing zone. An agitating gas stream can also be optionally employed to aid in the mixing of the two streams.

As a further embodiment to this invention, mixing of the acid and water soluble silicate solution can be accomplished in a vessel equipped with mechanical means to create the necessary turbulence, such that mixing of the two streams is accomplished at a Reynolds number of greater than 4000. The vessel can optionally be equipped with baffles. The acid or the alkali metal aluminate and water soluble silicate solution can be but do not have to be fed to the vessel simultaneously.

To produce polyaluminosilicate microgels, a concentrated solution of an aluminum salt, preferably aluminum sulfate, is pumped from an additional reservoir and mixed into the diluted acid stream at a point before that at which the diluted acid and silicate streams are mixed and reacted. By the addition of the aluminum salt to the acid stream or by the use of aluminate directly, the rate of formation of microgel is increased and a polyaluminosilicate microgel is formed having aluminum moieties incorporated throughout the microgel structure.

The method and apparatus of the invention are capable of producing stable polysilicate and polyaluminosilicate microgels resulting in reduced silica deposition within a convenient time frame of not more than about 15–16 minutes, but usually within 30 to 90 seconds, without the risk of solidification and with minimum formation of undesirable silica deposits within the processing equipment. Temperature of operation is usually within the range of 0°–50° C.

Silica deposition in production apparatus is undesirable because it coats all internal surfaces of the apparatus and can impede the functioning of vital moving parts and instrumentation. For example, silica deposition can build to the point where valves can no longer function and can restrict fluid flow through pipes and tubing. Deposition of silica is also undesirable on the pH sensing electrode as it prevents monitoring the process pH, a critical quality control parameter for silica microgel production.

DETAILED DESCRIPTION OF THE INVENTION

Figure 1:
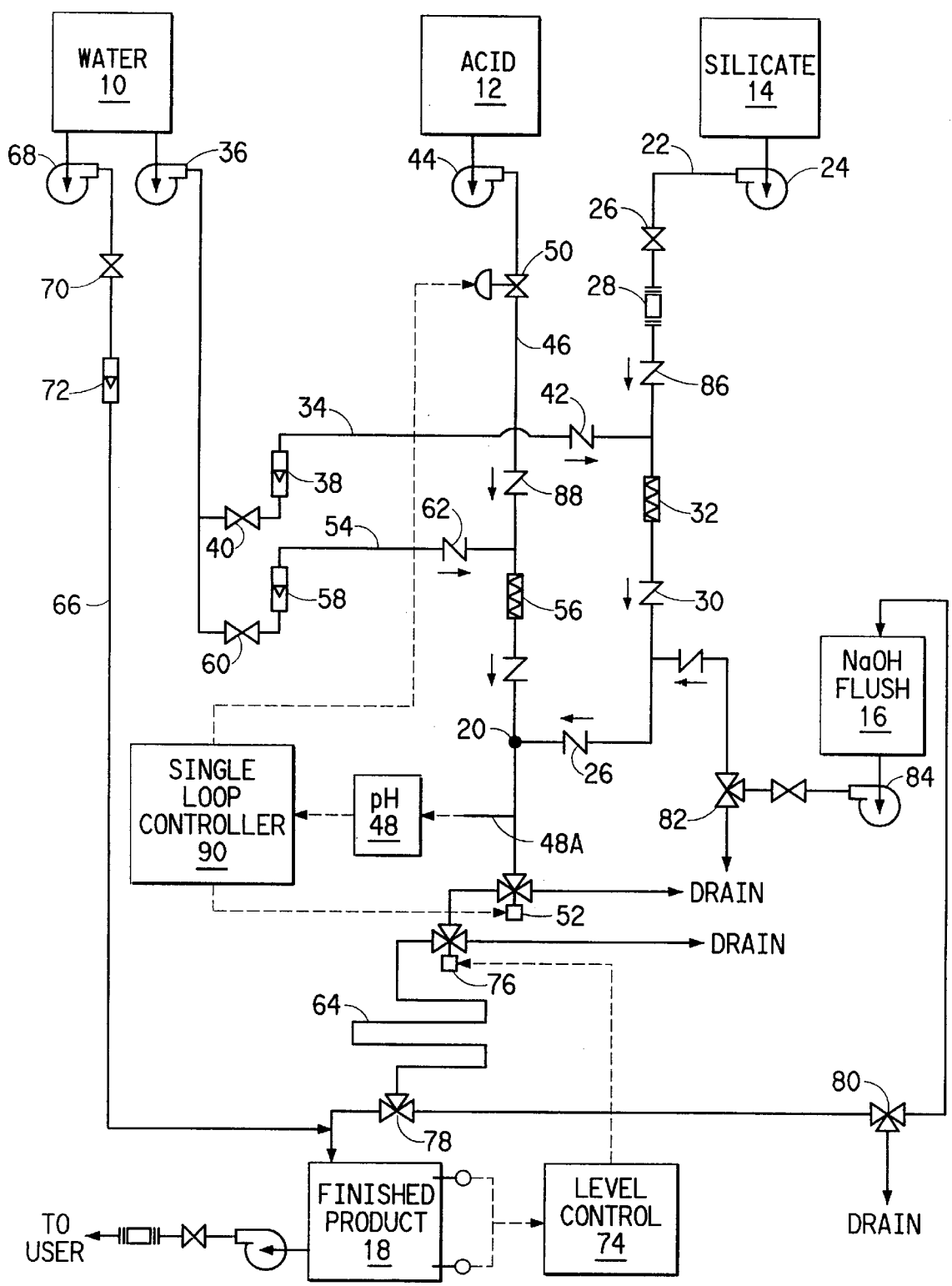
FIG. 1 is a schematic diagram of the process which includes a NaOH reservoir and means for periodically flushing the production system.

Active silica is a specific form of microparticulate silica comprising very small 1–2 nm diameter particles which are linked together in chains or networks to form three-dimensional structures known as "microgels". The surface area of the active silica microparticulates, i.e., the microgels, is at least about 1000 m$^2$/g. General methods for preparing polysilicate microgels are described in U.S. Pat. No. 4,954,220, the teachings of which are incorporated herein by reference. Of the methods described therein, the acidification of a dilute aqueous solution of an alkali metal silicate with an inorganic acid or organic acid, i.e., a strong acid having a pKa of less than 6, is the method to which this invention is particularly applicable. The present invention provides for the reliable and continuous preparation of low-concentration polysilicate and polyaluminosilicate microgels at the site of intended consumption without formation of undesirable silica deposits within the processing equipment and at very reasonable aging times generally less than 15 minutes, and preferably between from 10 to 90 seconds.

The method of the invention is carried out by simultaneously introducing a stream of a water soluble silicate solution and a stream of strong acid having a pKa less than 6, along with an aluminum salt or, alternatively, by mixing the silicate solution with an alkali metal aluminate into a mixing zone or mixing junction such that the streams converge at an angle of generally not less than 30 degrees. with respect to each other and at a rate which is sufficient to produce a Reynolds number in the region where the two streams converge of at least 4000, and preferably in the range of about 6000 and above. Reynolds number is a dimensionless number used in engineering to describe liquid flow conditions within a tube or pipe. Numbers below 2000 represent laminar flow (poor mixing environment) and numbers of 4000 and above represent turbulent flow (good mixing environment). As a general rule, the larger the Reynolds number the better the mixing. Reynolds number, (Re) for flow in a pipe or tube, is determined from the equation $$Re = \frac{Q \times d}{D \times u}$$

Where: Q=flow in cubic feet per second
d=Density in pounds per cubic foot
D=Pipe diameter in feet
u=Viscosity in pounds per foot second Reynolds number for impeller-stirred vessels is determined from the equation $$Re=(D^2 \times N \times p)/u$$

Where: D=Impeller diameter in cm
N=Rotational velocity in revolutions per second
p=Fluid density in grams per cm$^3$
u=Viscosity in grams per (second)(centimeter)

The concentrations of the converging silicate solution and the acid/aluminum salt streams are controlled so that the resulting silicate/acid mixture thus produced has a silica concentration in the range of 1 to 6 wt. % and a pH in the range of 2 to 10.5. Mixing of silicate solution and alkali metal aluminate is generally accomplished at pH>8 and most preferably at pH>10. More preferably the silica concentration is in the range of 1.5 to 3.5 wt. % and the pH is in the range of 7 to 10. The most preferred operating conditions are with a Reynolds number larger than 6000, a silica concentration of 2 wt. % and a pH of 9.

Aging is generally accomplished in from 10 up to about 90 seconds by passing the silicate/acid mixture through an elongated transfer loop in route to a finished product receiving tank in which the mixture is immediately diluted and thereafter maintained at an active silica concentration of not greater than 2.0 wt. % and, preferably, not greater than 1.0 wt. %. Partial gelation which produces the three-dimensional aggregate networks and chains of high surface area active silica particles is achieved during aging. Dilution of the silicate/acid or silicate/aluminate mixtures to low concentration operates to halt the gelation process and stabilize the microgel for subsequent consumption.

The method of the invention and an apparatus for carrying it out will now be discussed in greater detail in reference to the drawings in which FIG. 1 is a schematic diagram of the process in its simplest form to prepare polysilicate microgels. The sizes, capacities and rates described herein can be varied over wide ranges depending primarily on the quantities of polysilicate microgel or polyaluminosilicate required and the expected rate of consumption. The sizes and capacities described in reference to the drawings relate to a system for producing, i.e., generating, polysilicate or polyaluminosilicate microgels on a generally continuous basis for consumption as a drainage and retention aid in a papermaking process in which the consumption rate ranges from about 10 to 4000 lbs. microgel per hour.

There is shown in FIG. 1 a dilution water reservoir 10, an acid reservoir 12, and a silicate reservoir 14. The reservoirs, i.e., tanks, are conveniently made of polyethylene, with the water reservoir having a capacity of 500 gallons, the acid reservoir having a capacity of 100 gallons, and the silicate reservoir having a capacity of 300 gallons. Other vessels shown in FIG. 1 are NaOH flush tank 16 and finished product receiving tank 18. The NaOH flush tank is made of a non-corrosive material, such as, for example, 316 stainless steel; it has a capacity of 20 gallons and is heated with an electrical resistance drum heater wrapped around it (Cole-Palmer, 2000 watts, 115 volts). The finished product receiving tank has a capacity of 1000 gallons and is made of polyethylene.

A critical element of the process is mixing junction 20 which defines a mixing zone in which a stream of acid and a stream of water soluble silicate are introduced along individual paths which converge within the mixing zone at an angle generally not less than 30 degrees. A mixing "T" or "Y" junction is suitable for practicing the invention and may readily be constructed from an appropriately sized 316 stainless steel "Swagelok" compression coupling fitted with stainless steel tubing. A "T" junction is generally preferred.

The rates at which the two streams enter, i.e. are pumped into, the mixing zone are selected to produce a Reynolds number therewithin of at least 4000 and preferably up to 6000 or higher which results in practically instantaneous and thorough mixing of the acid and silicate such that the resulting mixture has a silica concentration in the range of from 1.5 to 3.5 wt. % and a pH of from 7 to 10. Any convenient commercial source of water soluble silicate can be employed, such as, for example, "PQ (N)" sodium silicate (41 Baume, SiO$_2$:Na$_2$O=3.22:1 by weight, 28.7 wt. % SiO$_2$) marketed by the PQ corporation. The commercial silicate is maintained undiluted in reservoir 14, usually at a concentration of 24 to 36 wt. % as supplied by the manufacturer, until it is needed. It is supplied to the mixing junction 20 via suitable tubing 22 (316 SS, ¼ inch OD) by means of a low flow rate gear or micropump 24 (e.g., Micropump Corp., model 140, max. flow 1.7 gpm). Non-corrosive materials of construction, e.g., 316 stainless steel, are preferred to avoid any risk of corrosion and subsequent contamination. The silicate supply line also includes flow control valve 26 (Whitey, 316 SS, ¼ inch needle), magnetic flow meter 28 (Fisher Porter, 316 SS, ¹⁄₁₀ inch size) and check valve 86 (Whitey, 316 SS, ¼ inch diameter) for controlling and monitoring the amount and direction of silicate flow. In operation, dilution water is introduced into the silicate supply line 22 at a convenient location upstream of the silicate/acid mixing junction 20 so as to adjust the silica concentration to a value in the range of from 2 to 10 wt. %. To insure complete mixing of silicate and water an in-line static mixer 32 (Cole-Palmer, 316 SS, ½ inch tubing, 15 elements) is provided followed by a check valve 30 (Whitey, 316 SS, ½ inch diameter). The dilution water is supplied via line 34 (½ inch OD, 316 SS) by centrifugal pump 36 (Eastern Pump, 1 HP, max. flow 54 gpm), and a rotameter 38 (Brooks, Brass Ball, 3.06 gpm max.). Control valve 40 (Whitey, 316 SS, ½ inch NE needle) and check valve 42 (Whitey, 316 SS, ½ inch diameter) can be employed to the control flow rate and direction.

Although a wide range of acidic materials, such as, for example, mineral acids, organic acids, acid salts and gases, ion-exchange resins and the salts of strong acids with weak bases, have been described for use in preparing active silica, the simplest and most convenient means of acidification is with a strong acid having a pKa less than 6. The preferred acid is sulfuric acid. Commercial grades manufactured by DuPont and others are generally suitable. In operation, a stock solution of acid is maintained at a concentration in the range of from 5 to 100 wt. % in acid reservoir 12. The acid is pumped using a gear or similar micropump 44 (e.g., Micropump model 040, ¼HP, max. flow 0.83 gpm) to junction mixer 20 through line 46 (316 SS, ¼ inch OD) and check valve 88 (Whitey, 316 SS, ¼ inch diameter). A single loop controller 90 (Moore, Model 352E) is combined with pH transmitter 48 (Great Lakes Instruments, Model 672P3FICON) and pH Probe 48A (Great Lakes Instruments, Type 6028PO) to regulate the flow of acid to junction mixer 20 via automatic flow control valve 50 (Research Controls, K Trim, ¼ inch OD, 316 SS) in response to the pH of the silicate/acid mixture measured at the exit of the junction mixer. An automatic three-way valve 52 (Whitey, 316 SS, ½ inch diameter) is also employed within the control system to allow for the possibility of having to divert off-spec. silicate/acid mixture to the sewer. Dilution water from water reservoir 10 is provided via line 54 (316 SS, ½ inch OD) to dilute the acid supply upstream of junction mixer 20 to a predetermined concentration in the range of from 1 to 20 wt. %. A static mixer 56 (Cole-Palmer, 316 SS, ½ inch diameter, 15 turns) is provided downstream of the point where dilution water is introduced into the acid supply line to insure complete mixing and dilution of the acid. A rotameter 58 (Brooks, Brass Ball, 1.09 gpm. maximum), control valve 60 (Whitey, 316 SS, ½ inch needle) and check valve 62 (Whitey, 316 SS, ½ inch diameter) are used to control flow rate and flow direction of the dilution water.

The silicate/acid mixture which exits junction mixer 20 has preferably a $SiO_2$ concentration in the range of from 1.5 to 3.5 wt. % and a pH in the range of from 7 to 10. Most preferably the silica concentration is maintained at 2 wt. % and the pH at 9. The mixture is passed through an elongated transfer line 64 (1½ inch schedule 40 PVC pipe, 75 feet in length) in route to finished product receiving tank 18. The length of the transfer line is selected to insure that the transfer will take at least 10 seconds, but preferably from about 30 seconds to 90 seconds, during which time "aging" or partial gelation of the mixture takes place. Transfer time can be as long as 15–16 minutes at very low flow rates and still produce satisfactory results. Dilution water from reservoir 10 is added via line 66 (316 SS, ½ inch OD) to the mixture just prior to its entry into finished product receiving tank 18 or at any other convenient location so long as the silicate/acid mixture is diluted to an $SiO_2$ concentration of less than 1.0 wt. % which stabilizes the gelation process. Dilution water is supplied with centrifugal pump 68 (Eastern, 316 SS, 1HP, 54 gpm maximum), and flow control is accomplished at a predetermined rate with control valve 70 (Whitey, 316 SS, ½ inch needle) and rotameter 72 (Brooks, SS Ball, 12.46 gpm maximum). The finished product receiving tank 18 is provided with a level control system 74 (Sensall, Model 502) which operates in conjunction with an automatic three-way valve 76 (Whitey, 316 SS, ½ inch diameter) to divert flow of the silicate/acid mixture to the sewer if the level of finished product becomes too high.

After a period of continuous operation, which depends on the amount of active silica produced, it may be desirable to cease generation of the active silica and flush the mixing junction 20 and that portion of the system which is downstream, i.e., piping, valves, transfer lines, etc., which have been in contact with the silicate/acid mixture, with water and warm NaOH. Flushing the system removes any undesirable silica deposits which may have accumulated in parts of the apparatus where the required turbulent flow conditions could not have been maintained due to design restrictions, as for example in the region of pH measurement. The flushing procedure helps maintain the system free of silica deposition and is begun by first shutting off dilution pump 68, acid pump 44 and silicate pump 24. Dilution water from pump 36 is then circulated through the downstream portion of the system for about 5 minutes, after which pump 36 is shut off, and the dilution water reservoir is isolated by closing valves 40, 60 and 70. Three-way automatic valves 52 and 76, and manual valves 78, 80 and 82 (all Whitey, 316 SS, ½ inch OD) are then activated along with centrifugal circulating pump 84 (Eastern, 316 SS, 1.5 HP, 15 gpm maximum) to allow NaOH, maintained at a concentration of 20 wt. % and a temperature in the range of from 40° to 60° C., to circulate through the downstream portion of the system for generally not longer than about 20–30 minutes. The NaOH circulating pump 84 and the flush tank 16 are then isolated from the system by again activating three-way valves 80 and 82, and dilution water is again flushed through the downstream system and released to the sewer. Having completed the cleaning/flushing procedure, the production of active silica can be resumed.

Figure 2:
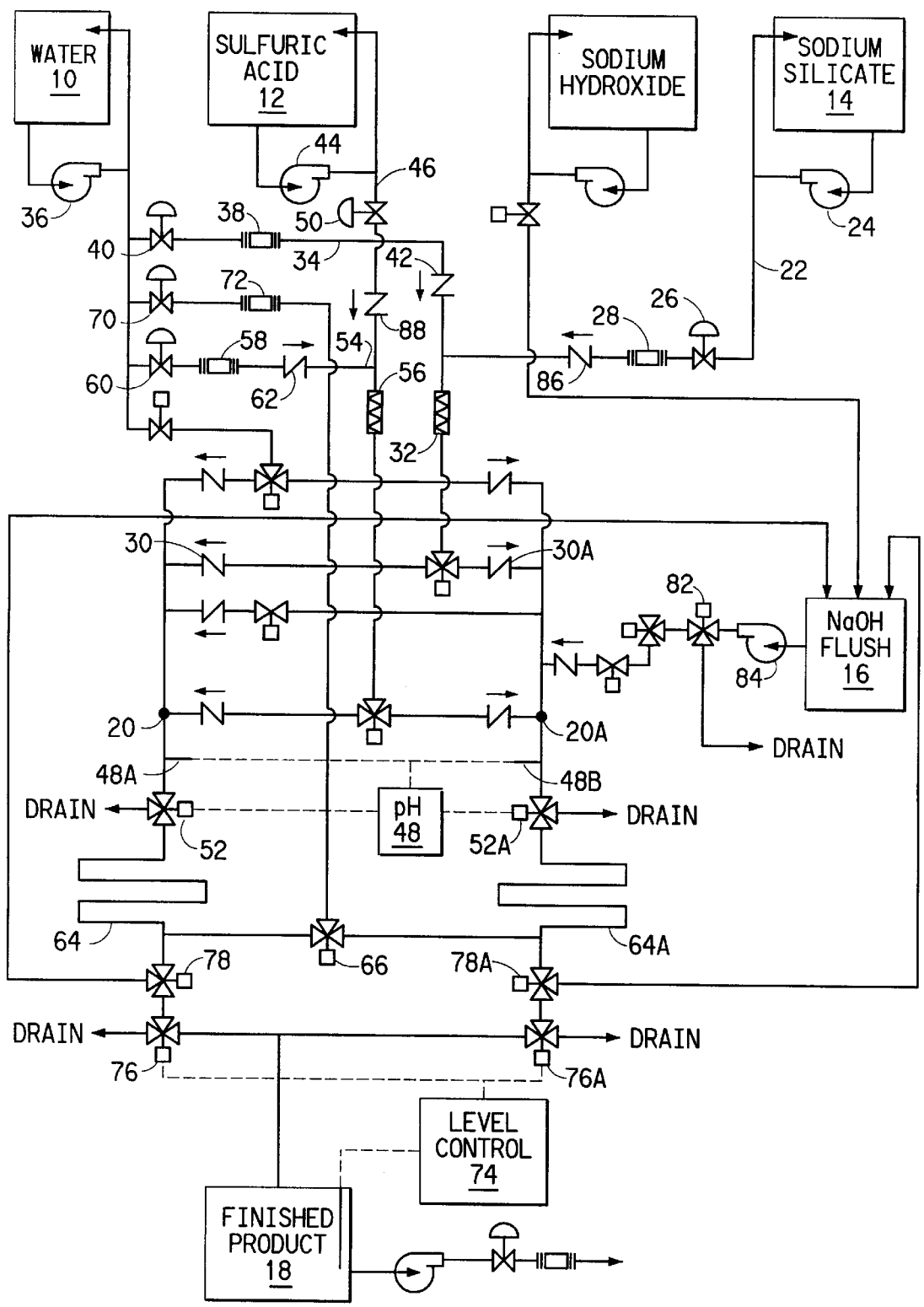
FIG. 2 is a schematic diagram of a dual line polysilicate microgel production system which provides for uninterrupted microgel production.

Referring now to FIG. 2, there is shown a schematic diagram of a dual line production system for active silica, whereby one line can be operational at all times while the other line is being flushed or being maintained in a stand-by condition. The component parts are numbered in accordance with FIG. 1. A commercial system according to either of FIGS. 1 or 2, will generally be constructed of stainless steel or polyvinyl chloride tubing of generally one inch diameter or less, depending on the requirement for active silica. When stainless steel tubing is used, connections of the various instruments, fittings, valves, and sections can be conveniently made with "Swagelok" compression joints.

Figure 3:
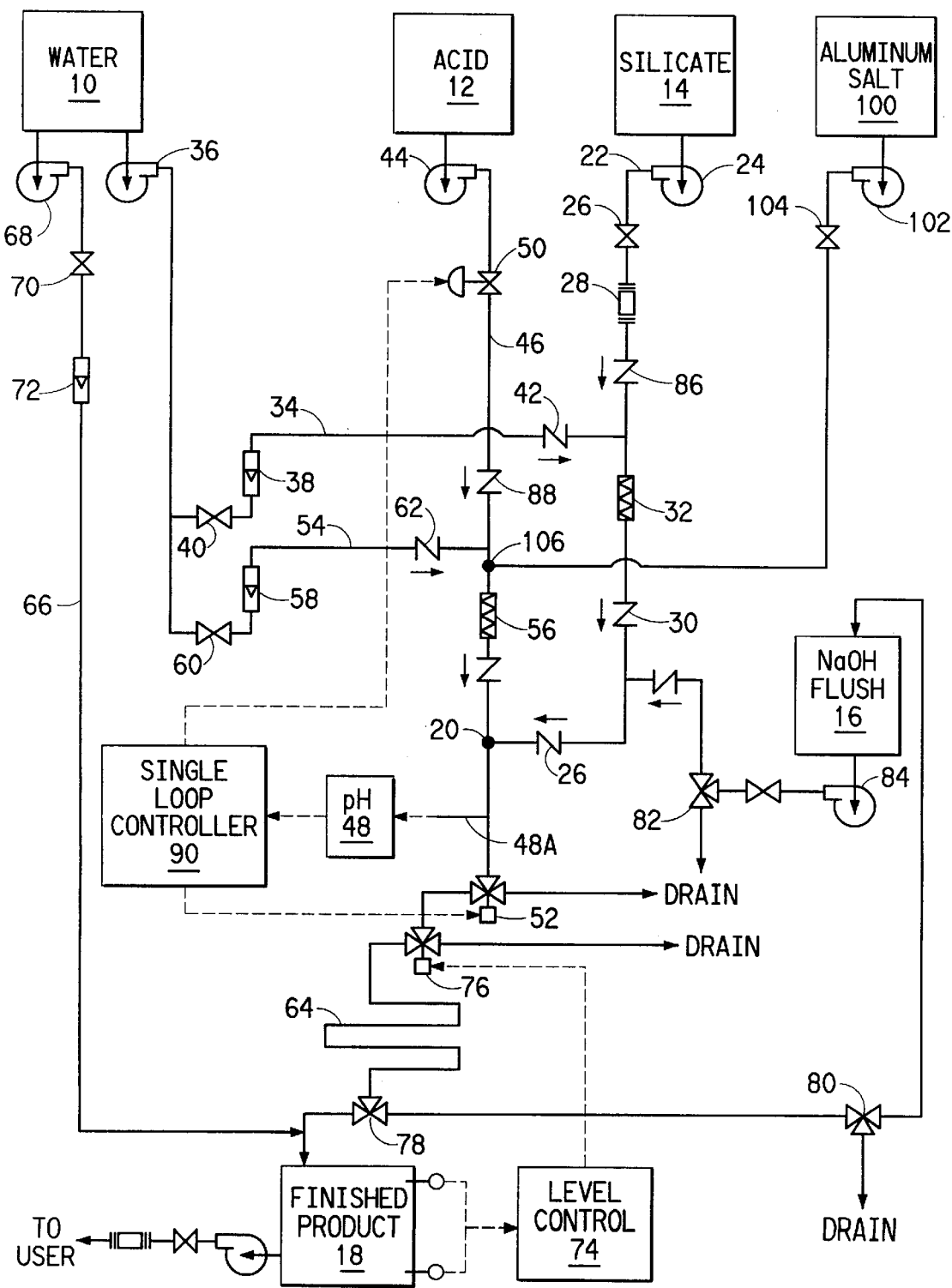
FIG. 3 is a schematic diagram of the process of the invention for the production of polyaluminosilicate microgels which includes an aluminum salt reservoir and means for introducing said salt into the dilute acid stream.

FIG. 3 is a schematic diagram showing a modification of the basic apparatus of FIG. 1 suitable for the production of polyaluminosilicate microgels. From the reservoir 100, a concentrated solution of an aluminum salt, preferably aluminum sulfate, can be pumped through tubing (¼ inch diameter 316 stainless steel) by means of a diaphragm metering pump 102 (Pulsatron® Model LPR 2-MAPTC1, glass filled polypropylene, Teflon® diaphragm, max. flow 12.5 ml/min). The metering pump 102 can be linked electronically to the controller 90 and can move in parallel with silicate usage. After passing through check valve 104 (Whitey, 316 SS, ¼ inch diameter), the aluminum salt solution can be introduced into the diluted acid line at the point 106 by means of a 316 SS "T" junction. Thorough mixing of the aluminum salt with the diluted acid can be completed by the in-line mixer 56 before reaction with the silicate, to produce polyaluminosilicate microgels, occurs at "T" junction 20. A preferred aluminum salt solution for use in the method is a commercial solution of aluminum sulfate such as liquid alum solution $Al_2(SO_4)_3, 14H_2O$ containing 8.3 wt. % $Al_2O_3$ supplied by the American Cyanamid Company.

Periodically, it is necessary to flush the polyaluminosilicate apparatus free from silica deposits by means of warm caustic soda solution as described above.

It should be understood that a dual line apparatus for the continuous production of polyaluminosilicate microgels can be constructed by the appropriate modifications of the dual line apparatus of FIG. 2.

Figure 4:
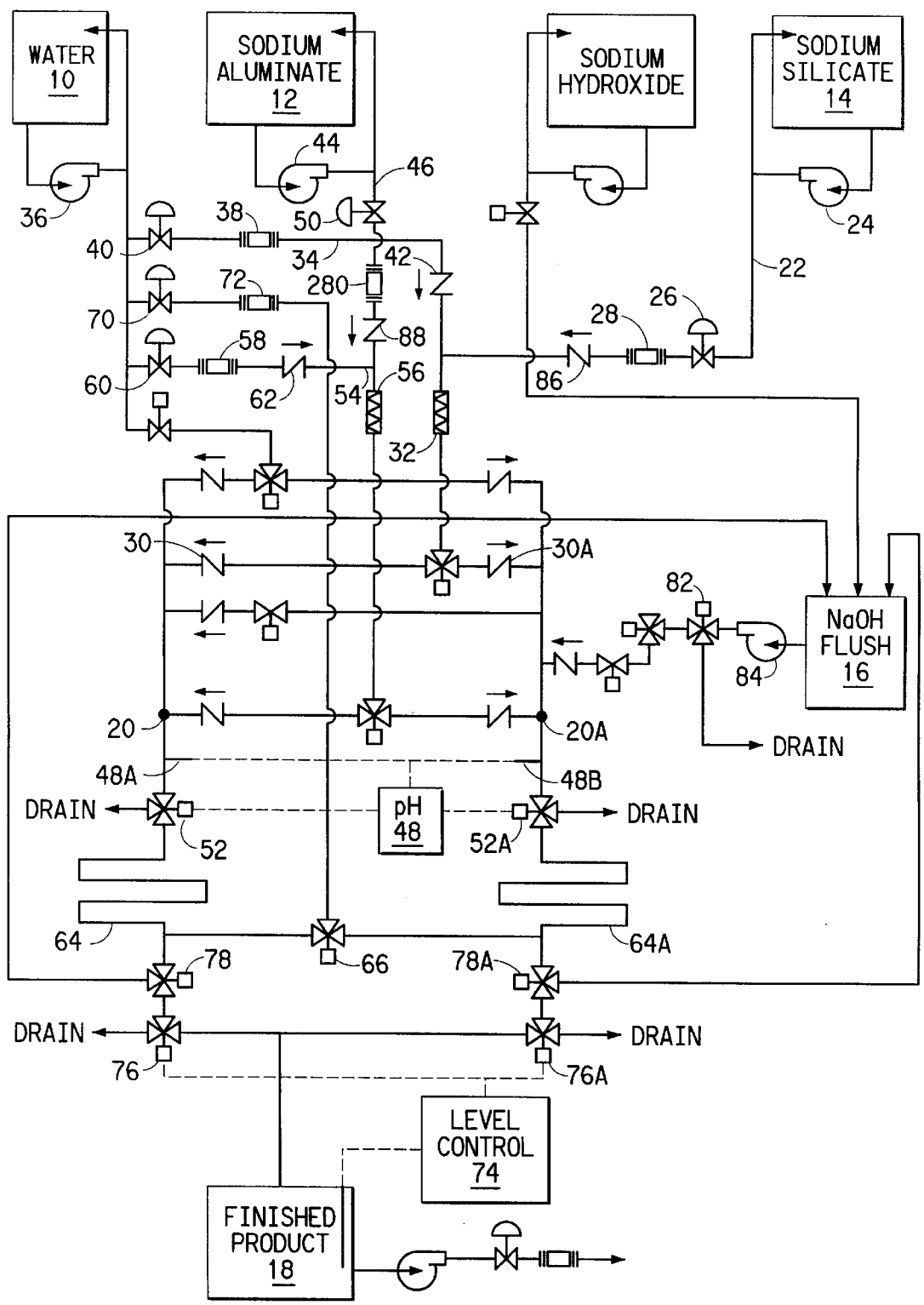
FIG. 4. is a schematic diagram of a dual line polyaluminosilicate microgel production system which provides for uninterrupted microgel production.

FIG. 4 is a schematic diagram showing a modification of the basic apparatus of FIG. 1 suitable for the production of polyaluminosilicate microgels prepared by mixing silicate with aluminate. Reservoir 12 contains an alkali metal aluminate solution, preferably sodium aluminate. The sodium aluminate solution can be prepared from dry sodium aluminate which is then dissolved in water or can be purchased as a predissolved and stabilized solution. The aluminate solution is supplied to the mixing junction using micropump 24. The aluminate supply line also includes flow control valve 50, and check valve 86. An additional magnetic flow meter 280 (Fisher Porter, 316 SS, 1/10 inch size) for monitoring the amount of aluminate flow can be added or aluminate flow can be controlled by varying the speed of micropump 24. Optionally, pH probes 48A and 48B and pH controller 48 can be eliminated. In operation, dilution water is introduced into the aluminate supply line 46 at a convenient location upstream of the silicate/aluminate mixing junction 20. To insure complete mixing of the aluminate and water an in-line static mixer 56 is provided. When mixed with the silicate stream, the resulting solution has a silica concentration in the range of from 2 to 10 wt %.

Periodically, it is necessary to flush the polyaluminosilicate apparatus free from silica deposits by means of warm caustic soda solution as described above.

EXAMPLE 1

Demonstrating the effect of turbulence in reducing silica deposition.

A laboratory generator for producing polysilicate microgels was constructed according to the principles described in FIG. 1. The silicate and sulfuric acid feeds, before dilution and mixing, contained 15 wt. % silica and 20 wt. % acid respectively. The critical junction mixer was constructed from a ¼ inch, 316 stainless steel "Swagelok" T-compression fitting fitted with 6 inch arms of ¼ inch OD 316 SS tubing. The internal diameter of the fitting was 0.409 cm. For the tests in which a gas was introduced into the mixing junction a similar "Swagelok" X-compression coupling was used with the fourth arm of the X as the gas inlet. An in-line filter comprised of 1 inch diameter 60 mesh stainless steel screen was placed about 12 inches from the acid/silicate junction to trap particulate silica. The screen was weighed at the beginning of each test and again at the end of each test, after washing and drying, so as to give a measure of silica deposition. All tests were run so as to maintain conditions of 2 wt. % silica and pH 9 at the point of silicate acidification and each test was run for sufficient time to produce a total amount of 1,590 gms. of polysilicate microgel. The results of the tests are given in Table 1 below. Liquid flow represents the total liquid flow, that is, the flow of the combined silicate/acid mixture in the exit tube. In the tests where a gas was introduced to enhance liquid flow and turbulence, the Reynolds number was calculated on the basis of the increased flow rate of the liquid portion alone, assuming that liquid density and viscosity did not change appreciably. This method of calculation was adopted because there is no ready formula for calculating the Reynolds number of liquid/gas mixtures.

TABLE 1

Silica Deposition As A Function Of Reynolds Number

| Test No. | Reynolds No. | Run Time mins. | Liquid Flow ml/m | Gas Flow ml/m | Silica deposited, gms. |
|---|---|---|---|---|---|
| 1 | 1,036 | 330 | 250 | none | 0.339 |
| 2 | 2,072 | 165 | 499 | none | 0.135 |
| 3 | 4,144 | 83 | 999 | none | 0.009 |
| 4 | 6,217 | 55 | 1,498 | none | 0.007 |
| 5 | 10,362 | 33 | 2,497 | none | 0.002 |
| 6 | 12,433 | 27 | 2,996 | none | 0.008 |
| 7 | 12,260 | 120 | 694 | Air, 2,260 | 0.008 |
| 8 | 9,064 | 120 | 694 | Air, 1,490 | 0.005 |

TABLE 1-continued

Silica Deposition As A Function Of Reynolds Number

| Test No. | Reynolds No. | Run Time mins. | Liquid Flow ml/m | Gas Flow ml/m | Silica deposited, gms. |
|---|---|---|---|---|---|
| 9 | 5,375 | 120 | 694 | Air, 601 | 0.004 |
| 10 | 5,375 | 120 | 694 | $N_2$, 601 | 0.014 |

A comparison of the results of Tests 1 & 2 with the results of Tests 3–10 clearly demonstrate the beneficial effect of turbulent liquid flow (Reynolds number above 4,000) in reducing the amount of silica deposition observed. Under turbulent flow conditions of the present invention, the average silica deposition of 0.007 g represented only 0.0004% of the total amount of silica processed. When the Reynolds number was below the minimum of 4,000 required by the instant invention, undesirable silica deposition was at least approximately 15-fold increased. Once the minimum Reynolds number required by the process of this invention was reached, increasing the Reynolds number above 4,000, for example from 4,144 to 6,217 to 10,362, etc. did not appreciably reduce silica deposition further.

EXAMPLE 2

Apparatus

A commercial sized apparatus for preparing active silica microgels was assembled according to the schematic design shown in FIG. 1 and installed in a commercial paper mill. The apparatus, except for the raw material supply reservoirs, was rigidly mounted on steel framework on two skids each measuring approximately six feet by eight feet. On skid 1 was mounted inlets for connection to commercial supplies of sodium silicate and sulfuric acid and an inlet for city water which was used for dilution purposes. Also on skid 1 was mounted the dilution and flow control means, the silicate/acid mixing junction, pH measurement and pH controller, sodium hydroxide flush reservoir, required pumps and valves and the electrical controls. On skid 2 was mounted the aging loop, finished product reservoir, level controller and required pumps and valves. Overall height of each skid was about seven feet. The manufacturers supply containers were used as reservoirs for the silicate and sulfuric acid and these were connected directly to the appropriate inlets on skid 1.

The apparatus was operated continuously for six (6) days during which 0.5 wt. % active silica was produced at a rate which varied between 3 and 4.8 gallons per minute. At a production rate of 3 gpm, a Reynolds number of 4250 was calculated for the mixing zone employed. No silica deposition was observed within the junction mixer 20, although some silica deposition was observed in the proximity of the pH probe located immediately downstream from the junction mixer exit after 12 hours of continuous operation. To alleviate this situation, a water/NaOH/water flush sequence was conducted, which took less than 30 minutes, and the system was then returned to normal production. Over the entire six day period, the apparatus operated without fault and produced active silica of excellent quality which was utilized by the mill for the production of a range of papers with different basis weights.

EXAMPLE 3

Preparation of Polyaluminosilicate Microgel

A commercial-sized apparatus for preparing polyaluminosilicate microgel solution was assembled according to the principles shown in FIG. 3. The apparatus, except for the raw material supply reservoirs, was rigidly mounted on steel framework on two skids each measuring approximately eight feet by eight feet. On skid 1 were mounted inlets for connection to supplies of sodium silicate, sulfuric acid, sodium hydroxide and papermaker's alum and an inlet for city water which was used for dilution purposes. Also mounted on skid 1 were the required pumps for each chemical and a reservoir for containing the finished polyaluminosilicate microgel solution. On skid 2 were mounted flow control valves for sodium silicate, acid, and the dilution water, the silicate/acid mixing junction, pH measurement means and pH controller, an aging loop, and a sodium hydroxide flush reservoir. Flow of the papermaker's alum was controlled by a diaphragm pump at rate proportional to the silicate flow. The papermaker's alum was introduced into the diluted acid stream prior to the silicate/acid mixing junction. The resulting polyaluminosilicate microgel solution had an $Al_2O_3/SiO_2$ molar ratio of approximately 1/1250.

The apparatus was used to produce 6000 gallons of 0.5 wt % polyaluminosilicate microgel solution at a rate of 20 gallons per minute. A Reynolds number of 22,700 was calculated for the mixing zone. Only minor silica deposition was noted on the pH electrode after 5 hours of operation. To remove the silica deposits, a NaOH flush was conducted, which took less than 30 minutes, and the system was then returned to normal production. The polyaluminosilicate microgel solution was utilized by a paper mill for the production of liquid packaging board with excellent results.

EXAMPLE 4
Preparation of Polyaluminosilicate Microgel

A commercial-sized apparatus for preparing polyaluminosilicate microgel solution was assembled according to the principles shown in FIG. 4. The apparatus, except for the raw material supply reservoirs, was rigidly mounted on steel framework on two skids each measuring approximately eight feet by eight feet. On skid 1 were mounted inlets for connection to supplies of sodium silicate, sodium aluminate and an inlet for city water which was used for dilution purposes. Also mounted on skid 1 were the required pumps for each chemical and a reservoir for containing the finished polyaluminosilicate microgel solution. On skid 2 were mounted flow control valves for sodium silicate and the dilution water, the silicate/aluminate mixing junction, an aging loop, and a sodium hydroxide flush reservoir. Flow of the sodium aluminate was controlled by a gear pump at rate proportional to the silicate flow. The sodium aluminate was diluted to 2 wt % $Al_2O_3$ prior to the silicate/aluminate mixing junction. The resulting polyaluminosilicate microgel solution had an $Al_2O_3/SiO_2$ molar ratio of approximately 1/10.

The apparatus was used to produce 450 gallons of 1.7 wt % polyaluminosilicate microgel solution at a rate of 2.3 gallons per minute. A Reynolds number of 11,700 was calculated for the mixing zone. The silica deposits which occurred in the mixing zone were found to be soluble in warm caustic solution.

The resulting 1.7% polyaluminosilicate microgel solution was diluted with water to 0.5 wt % to stabilize the solution at 1 and 5 minutes after mixing the dilute sodium silicate and sodium aluminate solutions together.

The performance, as a papermaking retention and drainage aid, of the polyaluminosilicate microgel solution was demonstrated by comparison to 5 nm colloidal silica utilizing a paper furnish composed of 35% bleached kraft hardwood, 35% bleached kraft softwood, and 30% precipitated calcium carbonate. The paper furnish consistency was 0.3 wt % and the pH was 8.0. The furnish was mixed in a Britt Jar at 750 rpm. Cationic potato starch was added to the furnish at a dose rate of 15 lb/t of the solids content of the furnish. Polyaluminosilicate prepred as above was added to the furnish at a dose rate of 1 lb/t. As a control, 5 nm colloidal silica was added to the furnish at a dose rate of 2 lb/t. The order and timing of the addition was:

| Time (sec) | Step |
|---|---|
| 0 | Start mixer |
| 15 | Add starch |
| 30 | Add silica |
| 45 | Stop mixer, transfer to freeness tester. |

After the chemicals were added to the furnish, the freeness of the furnish was determined using a Canadian Standard Freeness apparatus; the results are shown in Table 2 below (dose rates are given as lb of $SiO_2$ per ton of furnish solids):

TABLE 2

| | Freeness of Furnish | |
|---|---|---|
| Silica Used | Dose Rate (lb/t) | Freeness (ml) |
| colloidal silica (5 nm particle size) polyaluminosilicate microgel-aged for | 2 | 650 |
| 1 min. | 1 | 640 |
| 5 min. | 1 | 660 |

As can be seen from the above data, only approximately one-half as much silica, in the form of the polyaluminosilicate of this invention, was necessary to achieve the level of freeness as was required by the silica of the prior art.

We claim:

1. A method for continuously preparing a polyaluminosilicate microgel resulting in reduced silica deposition in which the microgel comprises a solution of from 1 to 2 nm diameter silica particles having a surface area of at least about 1000 $m^2/g$ which are linked together into individual chains to form three-dimensional network structures and comprises:

(a) simultaneously introducing a first stream comprising a water soluble silicate solution and a second stream comprising an alkali metal aluminate into a mixing zone where the streams converge at an angle of not less than 30 degrees and at a rate sufficient to produce a Reynolds number in the mixing zone of at least about 4000 and a resulting silicate/acid/salt mixture having a silica concentration in the range of from 1 to 6 wt. % and a pH>8;

(b) aging the silicate/aluminate mixture for a period of time sufficient to achieve a desired level of partial gelation, but not longer than 15 minutes; and (c) diluting the aged mixture to a silica concentration of not greater than 2.0 wt. %.

2. A method for continuously preparing a polyaluminosilicate microgel resulting in reduced silica deposition in which the microgel comprises a solution of primary silica particles of from 1 to 2 nm diameter silica particles having a surface area of at least about 1000 m$^2$/g which are linked together into individual chains to form three-dimensional network structures and comprises:

(a) simultaneously introducing a first stream comprising a water soluble silicate solution and a second stream comprising an alkali metal aluminate salt into an annular mixing device where the streams converge by the discharge of one stream from an internal pipe of the mixing device into the second stream flowing through an external pipe at a rate sufficient to produce a Reynolds number in the mixing zone of the mixing device of at least about 4000 and a resulting silicate/aluminate mixture having a silica concentration in the range of from 1 to 6 wt. % and a pH>8;

(b) aging the silicate/aluminate mixture for a period of time sufficient for the primary silica particles to link together and form said three-dimensional structures while remaining in solution, but not longer than 15 minutes; and (c) diluting the aged mixture to a silica concentration of not greater than 2.0 wt. %.

3. The method of claims 1 or 2 wherein said silica concentration is not greater than 1.0 wt. %.

\* \* \* \* \*